United States Patent
Krotz et al.

(10) Patent No.: US 7,273,933 B1
(45) Date of Patent: Sep. 25, 2007

(54) METHODS FOR SYNTHESIS OF OLIGONUCLEOTIDES

(75) Inventors: Achim H. Krotz, Irvine, CA (US); Vasulinga T. Ravikumar, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 950 days.

(21) Appl. No.: 09/032,972

(22) Filed: Feb. 26, 1998

(51) Int. Cl.
C07H 21/00 (2006.01)
C07H 21/04 (2006.01)

(52) U.S. Cl. .................. 536/25.31; 536/25.3; 536/24.3

(58) Field of Classification Search ............. 536/25.34, 536/24.3, 25.3, 25.31
See application file for complete search history.

(56) References Cited

U.S. PATENT DOCUMENTS

| | | | | |
|---|---|---|---|---|
| 3,687,808 | A | 8/1972 | Merigan et al. ............ | 435/91.3 |
| 4,415,732 | A | 11/1983 | Caruthers et al. .......... | 536/26.5 |
| 4,458,066 | A * | 7/1984 | Caruthers et al. ........ | 536/25.34 |
| 4,500,707 | A * | 2/1985 | Caruthers et al. .......... | 536/26.7 |
| 4,517,338 | A | 5/1985 | Urdea et al. ................ | 536/25.3 |
| 4,668,777 | A | 5/1987 | Caruthers et al. .......... | 536/26.5 |
| 4,725,677 | A | 2/1988 | Köster et al. ............. | 536/25.34 |
| 4,816,571 | A | 3/1989 | Andrus et al. .............. | 536/25.3 |
| 4,973,679 | A * | 11/1990 | Caruthers et al. ........ | 536/25.34 |
| 5,026,838 | A * | 6/1991 | Nokiri et al. ............... | 536/26.7 |
| 5,132,418 | A * | 7/1992 | Caruthers et al. ........ | 536/25.34 |
| RE34,069 | E * | 9/1992 | Köster et al. ............ | 536/25.33 |
| 5,151,510 | A | 9/1992 | Stec et al. ................. | 536/25.3 |
| 5,210,264 | A | 5/1993 | Yau ............................ | 558/167 |
| 5,212,295 | A | 5/1993 | Cook ........................ | 536/26.7 |
| 5,216,141 | A * | 6/1993 | Benner .................... | 536/27.13 |
| 5,292,875 | A | 3/1994 | Stec et al. ............... | 536/25.33 |
| 5,510,476 | A * | 4/1996 | Ravikumar et al. ...... | 536/25.31 |
| 5,548,076 | A * | 8/1996 | Froehler et al. .......... | 536/25.34 |
| 5,554,746 | A * | 9/1996 | Ravikumar et al. ......... | 540/200 |
| 5,614,621 | A * | 3/1997 | Ravikumar et al. ...... | 536/25.34 |
| 5,705,621 | A * | 1/1998 | Ravikumar ................ | 536/23.1 |
| 5,714,597 | A * | 2/1998 | Ravikumar et al. ...... | 536/25.31 |
| 6,538,128 | B1 | 3/2003 | Zhang et al. .............. | 536/25.3 |

FOREIGN PATENT DOCUMENTS

EP    0 294 196    12/1988

OTHER PUBLICATIONS

Ravikumar et al. (V), "Efficient Synthesis of Deoxyribonucleotide Phosphorothioates by the Use of DMT Cation Scavenger," *Tetrahedron Letters*, 36(37), 6587-6590 (Sep. 11, 1995).*
Krotz et al.(I), "Synthesis and Deprotection of β-Silylethyl Protected O, O, O- and O, O, S-Trialkylphosphorothioates," *Tetrahedron Letters*, 37(12), 1999-2002 (Mar. 1, 1996).*
Krotz et al. (II), "Phosphorothioate Oligonucleotides: Largely Reduced (N-1)-Mer and Phosphodiester Content Through the Use of Dimeric Phosphoramidite Synthons," *Bioorganic & Medicinal Chemistry Letters*, 7(1), 73-78 (Jan. 7, 1997).*
Krotz et al. (III), "Phosphorothioates: β-Fragmentation Versus β-Silicon Effect," *Angewandte Chemie Intl Ed.*, 34(21), 2406-2409 (Nov. 17, 1995).*
Sproat et al., "2'-O-Methyloligoribonucleotides: Synthesis and Applications," Ch. 3 in *Oligonucleotides and Analogues—A Practical Approach*, Eckstein (ed.), IRL Press, New York, NY, 1991, only title and text pp. 49-86 supplied, see especially p. 52.*
Connolly, "Oligonucleotides Containing Modified Bases," Ch. 7 in *Oligonucleotides and Analogues—A Practical Approach*, Eckstein (ed.), IRL Press, New York, NY, 1991, only title and text pp. 155-183 supplied , see especially p. 157.*
Conway et al., "Site-Specific Attachment of Labels to the DNA Backbone," Ch. 9 in *Oligonucleotides and Analogues—A Practical Approach*, Eckstein (ed.), IRL Press, New York, NY, 1991, only title and text pp. 211-239 supplied, see especially p. 218.*
Atkinson et al., "Solid-Phase Synthesis of Oligonucleotides by the Phosphite Triester Method," Ch. 3 in *Oligonucleotide Synthesis—A Practical Approach*, Gait (ed.), IRL Press, Washington, DC, Jul. 1985, only title and text pp. 35-81 supplied, see especially p. 80.*
Sproat et al.. "Solid-Phase Synthesis of Oligodeoxynucleotides by the Phosphotriester Method," Ch. 4 in *Oligonucleotide Synthesis—A Practical Approach*, Gait (ed.), IRL Press, Washington, DC, Jul. 1985, only title and text pp. 83-115 supplied , see especially p. 111.*
Gait, "An Introduction to Modern Methods of DNA Synthesis," Ch. 1 in *Oligonucleotide Synthesis—A Practical Approach*, Gait (ed.), IRL Press, Washington, DC, 1984, only pp. 1-22 and index/titled supplied.*
Septak, "Kinetic Studies on Depurination and Detritylation of CPG-Bound Intermediates During Oligonucleotide Synthesis," *Nucleic Acids Research*, 24(15), 3053-3058 (1996).*
Krotz et a.(I), "Synthesis and Deprotection of β-Silylethyl Protected O, O, O- and O, O, S-Trialkylphosphorothioates," *Tetrahedron Letters*, 37(12), 1999-2002 (Mar. 18, 1996).*
Sproat et al.(I), "2'-O-Methyloligoribonucleotides: Synthesis and Applications," Ch. 3 in *Oligonucleotides and Analogues—A Practical Approach*, Eckstein (ed.), IRL Press, New York, NY, 1991, only title and text pp. 49-86 supplied, see especially p. 52.*
Sproat et al.(II), "Solid-Phase Synthesis of Oligodeoxynucleotides by the Phosphotriester Method," Ch. 4 in *Oligonucleotide Synthesis—A Practical Approach*, Gait (ed.), IRL Press, Washington, DC, Jul. 1985, only title and text pp. 83-115 supplied , see especially p. 111.*
Horn et al.(III), "[title unknown]," *Nucleosides and Nucleotides*, 8(?), 875-877 (1989); copy ordered by interlibrary loan; Chem. Abstract citation could not be identified.*
Horn et al.(I), "Solid Support Hydrolysis of Apurinic Sites in Synthetic Oligonucleotides for Rapid and Efficient Purification on Reverse-Phase Cartridges," *Nucleic Acids Research*, 16(24), 11559-11571 (Dec. 23, 1988).*

(Continued)

*Primary Examiner*—Patrick Lewis
(74) *Attorney, Agent, or Firm*—Woodcock Washburn LLP

(57) ABSTRACT

Improved methods for synthesis of oligonucleotides and other phosphorus-linked oligomers are disclosed. The methods include the use of aromatic solvents, alkyl aromatic solvents, halogenated aromatic solvents, halogenated alkyl aromatic solvents, or aromatic ether solvents to achieve deprotection of protected hydroxyl groups.

42 Claims, No Drawings

OTHER PUBLICATIONS

Horn et al.(II), "Chemical Synthesis and Characterization of Branched Oligodeoxyribonucleotides (bDNA) for Use as Signal Amplifiers in Nucleic Acid Quantification Assays," *Nucleic Acids Research*, 25(23), 4842-4849 (Dec. 1, 1997).*

Horn et al.(III), "The Synthesis of Branched Oligonucleotides as Signal Amplification Multimers for Use in Nucleic Acid Assays,", *Nucleosides and Nucleotides*, 8(5&6), 875-877 (Jul./Sep. 1989).*

Alul, R.H. et al., "Oxalyl-CPG: a labile support for synthesis of sensitive oligonucleotide derivatives", *Nuc. Acid Res.*, 1991, 19, 1527-1532(Issue No. 7).

Berner, S. et al., "Studies on the role of tetrazole in the activation of phosphoramidites", *Nucl. Acids Res.*, 1989, 17, 853-864 (Issue No. 3).

Bielinska, A. et al., "Regulation of Gene Expression with Double-Stranded Phosphorothioate Oligonucleotides", *Science*, 1990, 250, 997-1000 (Nov. 16, 1990).

Brill, W.K. et al., "Synthesis of of oligodeoxynucleoside phosphorodithioates via thioamidites", *J. Am. Chem. Soc.*, 1989, 111, 2321-2322.

Brill, W.K.D. et al., "Synthesis of Deoxydinucleoside Phosphorodithioates", *J. Am. Chem. Soc.*, 1991, 113, 3972-3980 (Issue No. 10).

Brown, T. et al., "Modern machine-aided methods of oligodeoxyribonucleotide synthesis", *Oligonucleotides and Analogs*, Ekstein, F., ed., IRL Press, 1991, Chapter 1, 1-24.

Cook, P.D., "Medicinal chemistry of antisense oligonucleotides—future opportunities", *Anti-Cancer Drug Design*, 1991, 6, 585-607.

Dahl, B.H. et al., "Mechanistic studies on the phosphoramidite coupling reaction in oligonucleotide synthesis. I. Evidence for nucleophilic catalysis by tetrazole and rate variations with the phosphorus substituents", *Nucl. Acids Res.*, 1987, 15, 1729-1743 (No. 4).

Dahl, O., "Preparation of Nucleoside Phosphorothioates, Phosphorodithioates and Related Compounds", *Sulfur Reports*, 1991, 11(I), 167-192.

Delgado, C. et al., "The Uses and Properties of PEG-Linked Proteins", *Crit. Rev. in Therapeutic Drug Carrier Sys.*, 1992, 9, 249-304 (Issue No. 3-4).

Eckstein, F., "Nucleoside Phosphorothioates", *Ann. Rev. Biochem.*, 1985, 54, 367-402.

Efimov, V.A. et al., "New efficient sulfurizing reagents for the preparation of oligodeoxyribonucleotide phosphorothioate analogues", *Nucl. Acids Res.*, 1995, 23, 4029-4033 (Issue No. 20).

Englisch, U. et al., "Chemically Modified Oligonucleotides as Probes and Inhibitors", *Angew. Chem. Int. Ed. Eng.*, 1991, 30, 613-629 (No. 6, Jun. 1991).

Iyer, R.P. et al., "3H-1,2-Benzodithiole-3-one 1,1-Dioxide as an Improved Sulfurizing Reagent in the Solid-Phase Synthesis of Oligodeoxyribonucleoside Phosphorothioates", *J. Am. Chem. Soc.*, 1990, 112, 1253-1254.

Iyer, R.P. et al., "The Automated Synthesis of Sulfur-Containing Oligodeoxyribonucleotides Using 3H-1,2-Benzodithiol-3-one 1,1-Dioxide as a Sulfure-Transfer Reagent", *J. Org. Chem.*, 1990, 55, 4693-4699 (Issue No. 15).

Kamer, P.C.J. et al., "An Efficient Approach Toward the Synthesis of Phosphorothioate Diesters via the Schonberg Reaction", *Tetrahedron Letts.*, 1989, 30, 6757-6760 (Issue No. 48).

Kresse, J. et al., "The use of S-2-cyanoethyl phosphorothioate in the preparation of oligo 5'-deoxy-5'-thiothymidylates", *Nucl. Acids Res.*, 1975, 2(1), 1-9 (Jan. 1975).

Kroschwitz, J.I. (ed.), "Polynucleotides", *Concise Encyclopedia of Polymer Science and Engineering*, John Wiley & Sons, New York, 1990, 858-859.

Nielsen, J. et al., "Thermal Instability of Some Alkyl Phosphorodiamidites", *J. Chem. Res.*, 1986, S, 26-27.

Ouchi, T. et al., "Synthesis and Antitumor Activity of Poly(Ethylene Glycol)s Linked to 5'-Fluorouracil via a Urethane or Urea Bond", *Drug Des. & Disc.*, 1992, 9, 93-105.

Rao, M.V. et al., "Dibenzoyl Tetrasulphide-A Rapid Sulphur Transfer Agent in the Synthesis of Phosphorothioate Analogues of Oligonucleotides", *Tetrahedron Letts.*, 1992, 33, 4839-4842 (Issue No. 33).

Ravasio, N. et al., "Selective Hydrogenations Promoted by Copper Catalysts. 1. Chemoselectivity, Regioselectivity, and Stereoselectivity in the Hydrogenation of 3-Substituted Steroids", *J. Org. Chem.*, 1991, 56, 4329-4333 (Issue No. 13).

Secrist, J.A. et al., "Synthesis and Biological Activity of 4'-Thionucleosides", *10th International Rountable: Nucleosides, Nucleotides and their Biological Applications*, Sep. 16-20, 1992, Abstract 21, Park City, Utah, 40.

Sekine, M. et al., "Synthesis and Properties of S,S-Diaryl Nucleoside Phosphorodithioates in Oligonucleotide Synthesis", *J. Org. Chem.*, 1979, 44(13), 2325-2326.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005-3008 (Issue No. 26).

Wright, P. et al., "Large Scale Synthesis of Oligonucleotides via phosphoramidite Nucleosides and a High-loaded Polystyrene Support", *Tetrahedron Letts.*, 1993, 34, 3373-3376 (Issue No. 21).

Wu, H. et al., "Inhibition of in vitro transcription by specific double-stranded oligodeoxyribonucleotides", *Gene*, 1990, 89, 203-209.

Xu, Q. et al., "Efficient introduction of phosphorothioates into RNA oligonucleotides by 3-ethoxy-1,2,4-dithiazoline-5-one (EDITH)", *Nucl. Acids Res.*, 1996, 24, 3643-3644 (Issue No. 18).

Xu, Q. et al., "Use of 1,2,4-dithiazolidine (DtsNH) and 3-ethoxy-1,2,4-dithiazoline-5-one (EDITH) for synthesis of phosphorothioate-containing oligodeoxyribonucleotides", *Nucl. Acids Res.*, 1996, 24, 1602-1607 (Issue No. 9).

Yau, E.K. et al., "Synthesis of Dinucleoside and Dinucleotide Phosphorodithioates Via a Phosphotriester Approach", *Tetrahedron Letts.*, 1990, 31, 1953-1956(Iss. No. 4).

U.S. Appl. No. 08/398,901, filed Mar. 6, 1995, Cook et al.

Nanda D. Sinha, "Large-Scale Oligonucleotide Synthesis Using the Solid-Phase Approach," Chapter 18, pp. 437-463, from Methods in Molecular Biology, vol. 20: Protocols for Oligonucleotides and Analogs, Edited by S. Agrawal, 1993 Humana Press Inc., Totowa, NJ.

Carlton H. Paul and A. Timothy Royappa, "Acid binding and detritylation during oligonucleotide synthesis," Nucleic Acids Research, 1996, vol. 24, No. 15, 3048-3052.

Horn et al., "Forks and Combs and DNA: the synthesis of branched oligonucleotides", *Nuc. Acids Research*, 1989, 17, pp. 6959-6967.

The EPO Supplementary European Search Report dated May 15, 2003 (EP 99 90 8511).

* cited by examiner

METHODS FOR SYNTHESIS OF OLIGONUCLEOTIDES

FIELD OF THE INVENTION

The present invention is directed to improved methods for synthesis of oligonucleotides and other phosphorus-linked oligomers, using aromatic solvents, alkyl aromatic solvents, halogenated aromatic solvents, halogenated alkyl aromatic solvents, or aromatic ether solvents. Oligomers synthesized using the methods of the invention are useful for diagnostic reagents, research reagents and in therapeutics.

BACKGROUND OF THE INVENTION

It is well known proteins are significantly involved in many of the bodily states in multicellular organisms, including most disease states. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the production of such proteins is desired. By interfering with the production of proteins, the maximum therapeutic effect might be obtained with minimal side effects. It is the general object of such therapeutic approaches to interfere with or otherwise modulate gene expression which would lead to undesired protein formation.

One method for inhibiting specific gene expression is with the use of oligonucleotides, especially oligonucleotides which are complementary to a specific target messenger RNA (mRNA) sequence.

Transcription factors interact with double-stranded DNA during regulation of transcription. Oligonucleotides can serve as competitive inhibitors of transcription factors to modulate the action of transcription factors. Several recent reports describe such interactions (see Bielinska, A., et. al., *Science*, 1990, 250, 997–1000; and Wu, H., et. al., *Gene*, 1990, 89, 203–209).

In addition to functioning as both indirect and direct regulators of proteins, oligonucleotides have also found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligonucleotides, via Watson-Crick and/or Hoogsteen base pairs, to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in polymerase chain reactions (PCR) has given rise to an expanding commercial industry. PCR has become a mainstay of commercial and research laboratories, and applications of PCR have multiplied. For example, PCR technology is used in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in PCR technology.

Laboratory uses of oligonucleotides are described generally in laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA (see Book 2 of *Molecular Cloning, A Laboratory Manual*, ibid.) and DNA-Protein Interactions and The Polymerase Chain Reaction (see Vol. 2 of *Current Protocols In Molecular Biology*, ibid).

Oligonucleotides can be custom-synthesized for a desired use. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, (Tm)); to assist in identification of the oligonucleotide or an oligonucleotide-target complex; to increase cell penetration; to stabilize against nucleases and other enzymes that degrade or interfere with the structure or activity of the oligonucleotides; to provide a mode of disruption (terminating event) once sequence-specifically bound to a target; and to improve the pharmacokinetic properties of the oligonucleotides.

Thus, it is of increasing value to prepare oligonucleotides and other phosphorus-linked oligomers for use in basic research or for diagnostic or therapeutic applications. Consequently, and in view of the considerable expense and time required for synthesis of specific oligonucleotides, there has been a longstanding effort to develop successful methodologies for the preparation of specific oligonucleotides with increased efficiency and product purity.

Synthesis of oligonucleotides can be accomplished using both solution phase and solid phase methods. Oligonucleotide synthesis via solution phase in turn can be accomplished with several coupling mechanisms. However, solution phase chemistry requires purification after each internucleotide coupling, which is labor intensive and time consuming.

The current method of choice for the preparation of naturally occurring oligonucleotides, as well as modified oligonucleotides such as phosphorothioate and phosphorodithioate oligonucleotides, is via solid-phase synthesis wherein an oligonucleotide is prepared on a polymer support (a solid support) such as controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a polystyrene resin available from Perceptive Biosystems.

Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. The nucleotide phosphoramidites are reacted with the growing oligonucleotide using "fluidized bed" technology to mix the reagents. The known silica supports suitable for anchoring the oligonucleotide are very fragile and thus cannot be exposed to aggressive mixing. Brill, W. K. D., et al. *J. Am. Chem. Soc.*, 1989, 111, 2321, disclosed a procedure wherein an aryl mercaptan is substituted for the nucleotide phosphoramidite to prepare phosphorodithioate oligonucleotides on glass supports.

Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069.

While current solid-phase syntheses are suitable for preparing relatively small quantities of oligonucleotides, i.e., from about the micromolar (pmol) to millimolar (mmol) range, they typically are not amenable to the preparation of the larger quantities of oligonucleotides necessary for biophysical studies, pre-clinical and clinical trials and commercial production. Currently, to synthesize more than about three fourths of a mmol of oligonucleotide it is necessary to do sequential syntheses. A general review of solid-phase versus solution-phase oligonucleotide synthesis is given in the background section of Urdea, et al. U.S. Pat. No. 4,517,338, entitled "Multiple Reactor System And Method For Oligonucleotide Synthesis".

Large-scale preparation of oligonucleotides can be carried out by solution-phase techniques. One such solution phase preparation utilizes phosphorus triesters. Yau, E. K., et al., *Tetrahedron Letters*, 1990, 31, 1953, report the use of phosphorous triesters to prepare thymidine dinucleoside and thymidine dinucleotide phosphorodithioates The phosphorylated thymidine nucleoside intermediates utilized in the synthesis were obtained by treatment of commercially available 5'—O— dimethoxytritylthymidine-3'-[(β-cyanoethyl)-N,N-diisopropyl]-phosphoramidite first with either 4-chloro or 2,4-dichlorobenzylmercaptan and tetrazole, and then a saturated sulfur solution. The resulting phosphorodithioate nucleotide was then reacted via the triester synthesis method with a further thymidine nucleoside having a free 5'-hydroxyl.

Brill, W. K. D., et al., *J. Am. Chem. Soc.*, 1991, 113, 3972, disclose that treatment of a phosphoramidite such as N,N-diisopropyl phosphoramidite with a mercaptan such as 4-chloro or 2,4-dichlorobenzylmercaptan in the presence of tetrazole yields a derivative suitable for preparation of a phosphoro-dithioate as a major product and a derivative suitable for preparation of a phosphorithioate as a minor product.

Further details of methods useful for preparing oligonucleotides may be found in Sekine, M., etc al., *J. Org. Chem.*, 1979, 44, 2325; Dahl, O., *Sulfur Reports*, 1991, 11, 167–192; Kresse, J., et al., *Nucleic Acids Research*, 1975, 2, 1–9; Eckstein, F., *Ann. Rev. Biochem.*, 1985, 54, 367–402; and Yau, E. K. U.S. Pat. No. 5,210,264.

Methods for synthesizing oligonucleotides using intermediates having phosphorus-containing covalent linkages involve the protection of the 5'-hydroxyl group of a nucleoside by forming trityl or substituted trityl or triarylaklyl derivatives. The protecting groups are later removed under acidic conditions to yield the free 5'-hydroxyl group. The hydroxyl group can then be further reacted to give a coupled product.

The removal of trityl and other protecting groups is generally carried out in the presence of halogenated solvents such as dichloromethane or dichloroethane. However, the use of such halogenated solvents is undesirable for several reasons, particularly in relatively large scale applications such as the manufacture of oligonucleotides or analogs use as antisense agents. Consequently, there remains a need for methods of synthesis of oligonucleotides which provide improved efficiency and reduced disposal problems. The present invention is directed to these, as well as other, important ends.

SUMMARY OF THE INVENTION

The present invention provides improved methods for the preparation of oligonucleotides.

In some preferred embodiments the present invention provides methods for the preparation of a phosphorus-linked oligomer comprising the steps of:

(a) providing a solid support;

(b) attaching a 5'-O-protected nucleoside to the solid support;

(c) deprotecting the 5'-hydroxyl of the nucleoside with a deprotecting reagent comprising a protic acid in a solvent to deprotect the 5'-hydroxyl of the nucleoside, the solvent being an aromatic solvent, an alkyl aromatic solvent, a halogenated aromatic solvent, a halogenated alkyl aromatic solvent, or an aromatic ether solvent;

(d) reacting the deprotected 5'-hydroxyl with an 5'-protected activated phosphorus compound to produce a covalent linkage therebetween;

(e) oxidizing or sulfurizing the covalent linkage to form a phosphodiester, phosphorothioate, phosphorodithioate or H-phosphonate linkage;

(f) repeating steps c through e at least once for subsequent couplings of additional activated phosphorus compounds, to produce the completed phosphorus-linked oligomer; and (g) cleaving the oligomer from the solid support.

Some preferred embodiments of the methods of the invention further comprise the step of capping remaining reactive sites with a solution containing a capping reagent.

In some preferred embodiments, the oxidation or sulfurization step is performed after each iteration of steps (c) and (d). In other preferred embodiments, a single oxidation or sulfurization step is performed after the final iteration of steps (c) and (d).

In some preferred embodiments of the methods of the invention, solvent in step (c) is an aromatic solvent, an alkyl aromatic solvent, or an aromatic ether. In more preferred embodiments the solvent in step (c) is benzene, toluene, benzonitrile, o-, m- or p-xylene, mesitylene, or diphenyl ether, with benzene, toluene or o-, m- or p-xylene being more preferred, and toluene being particularly preferred.

In other preferred embodiments of the methods of the invention, the solvent in step (c) is a halogenated aromatic solvent or a halogenated alkyl aromatic solvent, with chlorobenzene or benzotrifluoride being especially preferred.

In some preferred embodiments of the methods of the invention the activated phosphorus compound is an activated mononucleotide, an activated dinucleotide, or an activated polynucleotide.

In further preferred embodiments of the method of the invention, the activated phosphorus compound is a 5'-protected nucleoside phosphoramidite or a 5'-protected activated H-phosphonate nucleoside.

In some preferred embodiments of the methods of the invention, the 5'-protecting group of the 5'-O-protected nucleoside and the 5'-protected activated phosphorus compound is independently trityl, monomethoxy trityl, dimethoxytrityl, trimethoxytrityl, 2-chlorotrityl, DATE, TBTr, Pixyl or Moxyl, with trityl, monomethoxy trityl, dimethoxy trityl, 9-phenylxanthine-9-yl (Pixyl) or 9-(p-methoxyphenyl)xanthine-9-yl (MOX) being more preferred, and dimethoxy trityl being especially preferred.

In some preferred embodiments of the methods of the invention, the phosphorus-linked oligomer is a phosphodiester, phosphorothioate phosphorodithioate, or H-phosphonate oligonucleotide.

In some preferred embodiments of the methods of the invention, the protic acid is formic acid, acetic acid, chloroacetic acid, dichloroacetic acid, trichloroacetic acid, trifluoroacetic acid, benzenesulfonic acid, toluenesulfonic acid, or phenylphosphoric acid.

In further preferred embodiments the solvent in step (c) further comprises an additive, which is preferably an alcohol, with from 0% to about 30% methanol, ethanol, 2-propanol, t-butyl alcohol, t-amyl alcohol, benzyl alcohol, or 1,1,1,3,3,3-hexafluoro-2-propanol, or a mixture thereof being especially preferred.

In some further preferred embodiments, the 5'-protected activated phosphorus compound is a 5'-protected activated H-phosphonate compound; and the phosphorus-linked oligomer is a H-phosphonate oligonucleotide.

In some preferred embodiments, the present invention provides methods for the preparation of a phosphorus-linked oligomer comprising the steps of:

a) providing a solid support;
b) attaching a 5'-O-protected nucleoside to the solid support;
c) contacting the protected 5'-hydroxyl of the nucleoside with a deprotecting reagent comprising a protic acid in a solvent to deprotect the 5'-hydroxyl of the nucleoside, the solvent being an aromatic solvent, an alkyl aromatic solvent, a halogenated aromatic solvent, a halogenated alkyl aromatic solvent, or an aromatic ether solvent;
d) reacting the deprotected 5'-hydroxyl with a 5'-protected activated phosphite compound to produce a phosphite linkage;
e) oxidizing or sulfurizing the phosphite linkage to form a phosphodiester, phosphorothioate, or phosphorodithioate linkage;
f) repeating steps c through e at least once for subsequent couplings of additional activated phosphite compounds, to produce the completed phosphorus-linked oligomer; and
g) cleaving the oligomer from the solid support.

Some preferred embodiments of the methods of the invention further comprise the step of capping remaining reactive sites with a solution containing a capping reagent.

In some preferred embodiments of the methods of the invention, solvent in step (c) is an aromatic solvent, an alkyl aromatic solvent, or an aromatic ether. In more preferred embodiments the solvent in step (c) is benzene, toluene, benzonitrile, o-, m- or p-xylene, mesitylene, or diphenyl ether, with benzene, toluene or o-, m- or p-xylene being more preferred, and toluene being particularly preferred.

In other preferred embodiments of the methods of the invention, the solvent in step (c) is a halogenated aromatic solvent or a halo aromatic solvent, with chlorobenzene or benzotirfluoride being especially preferred.

In some preferred embodiments of the methods of the invention the activated phosphorus compound is a mononucleotide phosphoramidite, a dinucleotide phosphoramidite, or a polynucleotide phosphoramidite.

In further preferred embodiments of the method of the invention, activated phosphorus compound is a 5'-protected nucleoside phosphoramidite or a 5'-protected activated H-phosphonate nucleoside.

In some preferred embodiments of the methods of the invention, the 5'-protecting group of the 5'-O-protected nucleoside and the 5'-protected activated phosphorus compound is independently trityl, monomethoxy trityl, dimethoxytrityl, trimethoxytrityl, 2-chlorotrityl, DATE, TBTr, Pixyl or Moxyl, with trityl, monomethoxy trityl, dimethoxy trityl, 9-phenylxanthine-9-yl (Pixyl) or 9-(p-methoxyphenyl)xanthine-9-yl (MOX) being more preferred, and dimethoxy trityl being especially preferred.

In some preferred embodiments of the methods of the invention, the phosphorus-linked oligomer is a phosphodiester, phosphorothioate or phosphorodithioate oligonucleotide.

In some preferred embodiments of the methods of the invention, the protic acid is formic acid, acetic acid, chloroacetic acid, dichloroacetic acid, trichloroacetic acid, trifluoroacetic acid, benzenesulfonic acid, toluenesulfonic acid, or phenylphosphoric acid.

In further preferred embodiments the solvent in step (c) further comprises an additive, which is preferably an alcohol, with from 0% to about 30% methanol, ethanol, 2-propanol, t-butyl alcohol, t-amyl alcohol, benzyl alcohol, or 1,1,1,3,3,3-hexafluoro-2-propanol, or a mixture thereof being especially preferred.

In some particularly preferred embodiments, the solvent in step (c) is benzene, toluene, benzonitrile, o-, m- or p-xylene, mesitylene, or diphenyl ether, with toluene being especially preferred; the activated phosphite compound is a mononucleotide phosphoramidite, a dinucleotide phosphoramidite, or a polynucleotide phosphoramidite; the protecting group of the 5'-O-protected nucleoside and the 5'-protected activated phosphite compound is dimethoxytrityl; the phosphorus linked oligomer is a phosphodiester, phosphorothioate or a phosphorodithioate oligonucleotide; and the protic acid is dichloroacetic acid.

DETAILED DESCRIPTION

The present invention provides novel methods for the preparation of phosphorus-linked oligomers comprising the steps of:

(a) providing a solid support;
(b) attaching a 5'-O-protected nucleoside to the solid support;
(c) deprotecting the 5'-hydroxyl of the nucleoside with a deprotecting reagent comprising a protic acid in a solvent to deprotect the 5'-hydroxyl of the nucleoside, the solvent being an aromatic solvent, an alkyl aromatic solvent, a halogenated aromatic solvent, a halogenated alkyl aromatic solvent, or an aromatic ether solvent;
(d) reacting the deprotected 5'-hydroxyl with an 5'-protected activated phosphorus compound to produce a covalent linkage therebetween;
(e) oxidizing or sulfurizing the covalent linkage to form a phosphodiester, phosphorothioate, phosphorodithioate or H-phosphonate linkage;
(f) repeating steps c through e at least once for subsequent couplings of additional activated phosphorus compounds, to produce the completed phosphorus-linked oligomer; and
(g) cleaving the oligomer from the solid support.

It is generally preferable to perform a capping step after reaction of the deprotected 5'-hydroxyl with an 5'-protected activated phosphorus compound. The capping step can be performed either before or after the oxidation or sulfurization step, and is generally known to provide benefits in the prevention of shortened oligomer chains, by blocking chains that have not reacted in the coupling cycle. One representative reagent used for capping is acetic anhydride. Other suitable capping reagents and methodologies can be found in U.S. Pat. No. 4,816,571.

The methods of the invention can be used for the preparation of a variety of phosphorus-linked oligonucleotide species, such as phosphodiester, phosphorothioate, phosphorodithioate and H-phosphonate oligonucleotides.

The methods of the invention can be used to prepare several types of oligonucleotides, including phosphodiesters, phosphotriesters, phosphorothioates, phosphodithioates, and H-phosphonates. These oligonucleotides are of the structure:

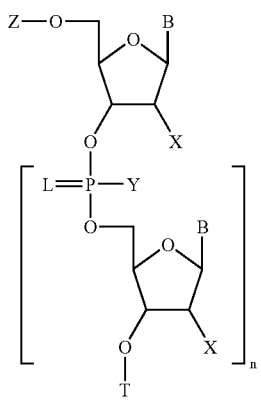

wherein Z is an acid labile protecting group and B is a naturally occurring nucleobase (i.e., adenine (A), cytosine (C), guanine (G), thymine (T) or uracil (U)) or any of the nucleobase analogs known in the art as described below. For the phosphodiester DNA, X=H, and B=A, C, G, or T; and for the phosphodiester RNA, X=OH, and B=A, C, G or U. Y is H, OH, SH or alkyl, and L is O or S. T is a solid support as described below for solid phase synthesis or a base labile protecting group for solution phase synthesis.

In the context of the present invention, the term "phosphorus-linked oligomer" refers to a plurality of joined nucleobase-bearing sugar moieties connected by a linking group having a phosphorus atom. Linking groups include phosphodiester, phosphotriester, phosphorothioate, phosphodithioate, and H-phosphonate linkages.

The structures listed above are representative of commonly synthesized phosphorus-linked oligomers, and the application of the methods of the present invention to them is illustrative, and not limiting. For example, it is known to substitute a wide variety of modifications on the above structures including base modifications, backbone modifications, phosphate modifications, sugar modifications, and 2' modifications. Recent modifications include replacing the sugar with an alternative structure which has primary and a secondary alcohol groups similar to those of ribose. As used herein, these modified compounds are included within the definition of the term "phosphorus-linked oligomers".

As used herein, the term "5'-protected activated phosphorus compound" is intended to denote a mono-, di- or polynucleoside species that has an activated phosphorus group at its 3'-terminus, and bears a 5'-hydroxyl protecting group. The activated phosphorus group is one that is known in the art to undergo a coupling reaction with the deprotected 5'-hydroxyl of a growing oligomeric chain according to standard synthetic methodologies, such as, for example, the phosphoramidite, phosphotriester and H-phosphonate synthetic methods. See for example Caruthers U.S. Pat. Nos. 4,415,732; 4,458,066; 4,500,707; 4,668,777; 4,973,679; and 5,132,418; and Koster U.S. Pat. No. 4,725,677 and Re. 34,069; Sekine, M., etc al., *J. Org. Chem.,* 1979, 44, 2325; Dahl, O., *Sulfur Reports,* 1991, 11, 167–192; Kresse, J., et al., *Nucleic Acids Research,* 1975, 2, 1–9; Eckstein, F., *Ann. Rev. Biochem.,* 1985, 54, 367–402; and Yau, E. K. U.S. Pat. No. 5,210,264, and *Oligonucleotides and Analogues A Practical Approach, Eckstein, F. Ed., IRL Press, New York,* 1991, each of the disclosures of which are hereby incorporated by reference in their entirety. Thus, activated phosphorus groups include groups of formula —P(—O—Pr)—N(i-pr)$_2$ where Pr is a phosphorus protecting group useful in phosphoramidite synthesis, such β-cyanoethyl.

In accordance with the methods of the invention, a 5'-O-protected nucleoside synthon is first attached to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069. Linkers are known in the art as short molecules which serve to connect a solid support to functional groups (e.g., hydroxyl groups) of initial synthon molecules in solid phase synthetic techniques. One such linker is a succinamide linker. Other suitable linkers are disclosed in, for example, *Oligonucleotides And Analogues A Practical Approach,* Ekstein, F. Ed., IRL Press, N.Y, 1991, Chapter 1, pages 1–23.

Solid supports according to the invention include those generally known in the art to be suitable for use in solid phase methodologies, including, for example, controlled pore glass (CPG), oxalyl-controlled pore glass (see, e.q., Alul, et al., *Nucleic Acids Research* 1991, 19, 1527), TENTAGEL Support (an aminopolyethyleneglycol derivatized support (see, e.g., Wright, et al., *Tetrahedron Letters* 1993, 34, 3373)) and POROS (a copolymer of polystyrene/divinylbenzene).

In accordance with the methods of the invention, after the initial nucleoside synthon is attached to the solid support, the 5'-hydroxyl of the nucleoside is deprotected with a deprotecting reagent, which includes a protic acid in a solvent, and, optionally, an additive.

Heretofore, deblocking of 5'-hydroxyl groups has been accomplished using such protic acids in a halogenated alkyl solvent such as dichloromethane or dichloroethane. However the use of such halogenated alkyl solvents is greatly disadvantageous because they are not easily disposed of (and therefore expensive to use) because of the environmental hazard they pose. For example, methylene chloride has been classified as a carcinogen by OSHA, and such low boiling solvents require a relatively large investment in recycling equipment.

It has been discovered in accordance with the present invention that deblocking reactions can be performed in solvents other than halogenated alkyl solvents. Thus, in accordance with preferred embodiments of the invention, deprotection (i.e, deblocking) of the 5'-O— protecting group is accomplished using a protic acid such as formic acid, acetic acid, chloroacetic acid, dichloroacetic acid, trichloroacetic acid, trifluoroacetic acid, benzenesulfonic acid, toluenesulfonic acid, or phenylphosphoric acid, in an aromatic solvent, an alkyl aromatic solvent, a halogenated aromatic solvent, a halogenated alkyl aromatic solvent, or an aromatic ether solvent.

In more preferred embodiments, the solvent is benzene, toluene, benzonitrile, o-, m- or p-xylene, mesitylene, or diphenyl ether. In still more preferred embodiments the solvent is benzene, toluene or o-, m- or p-xylene, with toluene being particularly preferred.

In some preferred embodiments, the solvent is high boiling; i.e., it has a boiling point greater than about 60° C. Such solvents are additionaly advantageous in that they do not require a substantial investment in recyling equipment that meets stringent environmental regulations required by OSHA for lower boiling solvents.

As used herein, the term alkyl includes but is not limited to straight chain, branch chain, and alicyclic hydrocarbon groups. Alkyl groups of the present invention may be substituted. Representative alkyl substituents are disclosed in U.S. Pat. No. 5,212,295, for example at column 12, lines 41–50, the disclosure of which is hereby incorporated by reference in its entirety.

The term aromatic solvent is intended to denote aromatic compounds that are known to be useful as solvents in the art. These include for example, substituted and unsubstituted benzene, pyrrole, furan, and tetrahydrofuran, where the substituents include halogen, nitro, or hydroxymethyl.

The term alkyl aromatic solvent is intended to denote aralalkyl compounds (i.e., compounds that have one or more alkyl groups attached to an aromatic ring) that are known to be useful as solvents in the art. These include for example, toluene, o-, m- or p-xylene, and mesitylene. Also included within the definition of "alkyl aromatic solvent" are liquid aromatic ring compounds that contain cyano groups, such as benzonitrile.

Halogens include fluorine, chlorine, bromine and iodine.

The term aromatic ether solvent is intended to mean a compound of formula R—O—R, wherein R is phenyl, halophenyl, or heteroaromatic, where the term heteroaromatic denotes an aromatic compound having at least one heteroatom (i.e., an atom other than carbon) in the aromatic ring.

The deprotected 5'-hydroxyl of the support bound nucleoside, or growing oligomeric chain, is then reacted with a the 5'-protected activated phosphorus compound to produce a covalent linkage therebetween. In some preferred embodiments wherein the activated phosphorus compound is a phosphoramidite, a phosphite linkage is produced. In other preferred embodiments, such as in H-phosphonate chemistries, the activated phosphorus group has the formula —O—HP(=O)—O—, and reacts with a free 3'-hydroxyl of the growing oligonucleotide chain in the presence of an activating agent such as pivaloyl chloride to produce an H-phosphonate linkage.

In some preferred embodiments, a sulfurization step or oxidation step is performed after each deprotection-coupling cycle. However, if desired, oxidation or sulfurization can be performed in a single step at the end of the iterative synthesis.

Useful oxidizing agents according to the present invention include iodine, t-butyl hydroperoxide, or other oxidizing reagents known in the art.

Sulfurizing agents used during oxidation to form phosphorothioate linkages include Beaucage reagent (see e.g. Iyer, R. P., et al., *J. Chem. Soc.*, 1990, 112, 1253–1254, and Iyer, R. P., et al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et al., *Tetrahedron Lett.*, 1992, 33, 4839–4842); di(phenylacetyl)disulfide (see e.g., Kamer, P. C. J., *Tetrahedron Lett.*, 1989, 30, 6757–6760); 1,2,4-dithiuazoline-5-one (DtsNH) and 3-ethoxy-1,2,4-dithiuazoline-5-one (EDITH) and (see Xu et al., *Nucleic Acids Research*, 1996, 24, 3643–3644 and Xu et al., *Nucleic Acids Research*, 1996, 24, 1602–1607); thiophosphorus compounds such as those disclosed in U.S. Pat. No. 5,292,875 to Stec et al., and U.S. Pat. No. 5,151,510 to Stec et al., disulfides of sulfonic acids, such as those disclosed in Efimov et al., *Nucleic Acids Research*, 1995, 23, 4029–4033, sulfur, sulfur in combination with ligands like triaryl, trialkyl, triaralkyl, or trialkaryl phosphines.

The deprotection and coupling steps, and, optionally, oxidation or sulfurization steps, are repeated using mono-, di- or polymeric activated synthons until the desired base sequence is achieved. The completed oligomer is then cleaved from the solid support. Cleavage is achieved by any of the standard methods in the art, such as, for example, with concentrated ammonium hydroxide.

The methods of the present invention can be used for the synthesis of phosphorus-linked oligonucleotides having both naturally occurring and non-naturally occurring constituent groups. For example, the present invention can be used to synthesize phosphodiester, phosphorothioate, phosphorodithioate, and H-phosphonate oligomers having naturally occurring pentose sugar components such as ribose and deoxyribose, and their substituted derivatives, as well as other sugars known to substitute therefor in oligonucleotide analogs.

The constituent sugars and nucleosidic bases of the phosphorus-linked oligonucleotides can be naturally occurring or non-naturally occurring. Non-naturally occurring sugars and nucleosidic bases are typically structurally distinguishable from, yet functionally inter-changeable with, naturally occurring sugars (e.g. ribose and deoxyribose) and nucleosidic bases (e.g., adenine, guanine, cytosine, thymine). Thus, non-naturally occurring nucleobases and sugars include all such structures which mimic the structure and/or function of naturally occurring species, and which aid in the binding of the oligonucleotide to a target, or which otherwise advantageously contribute to the properties of the oligonucleotide.

The methods of the invention are amenable to the synthesis of phosphorus-linked oligomers having a variety of substituents attached to their 2'-positions. These include, for example, halogens, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, the disclosure of which is hereby incorporated by reference. Further representative O-substitutions on the ribosyl ring include S, $CH_2$, CHF, and $CF_2$, see, e.g., Secrist, et al., *Abstract* 21, *Program & Abstracts, Tenth International Roundtable, Nucleosides, Nucleotides and their Biological Applications*, Park City, Utah, Sep. 16–20, 1992.

Representative nucleobases suitable for use in the methods of the invention include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and 7-methylguanine. Further naturally and non-naturally occurring nucleobases include those disclosed in U.S. Pat. No. 3,687,808 (Merigan, et al.), in chapter 15 by Sanghvi, in *Antisense Research and Application,* Ed. S. T. Crooke and B. Lebleu, CRC Press, 1993, in Englisch et al., *Angewandte Chemie,* International Edition, 1991, 30, 613–722 (see especially pages 622 and 623, and in the *Concise Encyclopedia of Polymer Science and Engineering,* J. I. Kroschwitz Ed., John Wiley & Sons, 1990, pages 858–859, Cook, P. D., *Anti-Cancer Drug Design,* 1991, 6, 585–607. The terms "nucleosidic base" and "nucleobase" are further intended to include heterocyclic compounds that can serve as nucleosidic bases, including certain 'universal bases' that are not nucleosidic bases in the most classical sense, but function similarly to nucleosidic bases. One representative example of such a universal base is 3-nitropyrrole.

The methods of the present invention use labile protecting groups to protect various functional moieties during synthesis. Protecting groups are used ubiquitously in standard oligonucleotide synthetic regimes for protection of several different types of functionality. In general, protecting groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. Representative protecting groups useful to protect nucleotides during synthesis include base labile protecting groups and acid labile protecting groups. Base labile protecting groups are used to protect the exocyclic amino groups of the heterocyclic nucleobases. This type of protection is generally achieved by acylation. Two commonly used acylating groups for this purpose are benzoylchloride and isobutyrylchloride. These protecting groups are stable to the reaction conditions used during oligonucleotide synthesis and are cleaved at approximately equal rates during the base treatment at the end of synthesis.

In some preferred embodiments, the 5'-protected activated phosphorus compound is a nucleoside phosphoramidite. Phosphoramidites of numerous nucleosides and derivatized solid supports are commercially available through various companies (e.g. Applied Biosystems Inc., Millipore Corp.). The amino moiety of such phosphordiamidites can be selected from various amines presently used for phosphoramidites in standard oligonucleotide synthesis. These include both aliphatic and heteroalkyl amines. One preferred amino group is diisopropylamino. Other examples of suitable amines as are described in various United States patents, principally those to M. Caruthers and associates. These include U.S. Pat. Nos. 4,668,777; 4,458,066; 4,415,732; and 4,500,707; all of which are herein incorporated by reference.

Hydroxyl protecting groups typically used in oligonucleotide synthesis may be represented by the following structure:

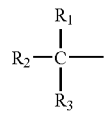

wherein each of $R_1$, $R_2$ and $R_3$ is an unsubstituted or mono-substituted aryl or heteroaryl group selected from phenyl, naphthyl, anthracyl, and five or six membered heterocylic rings with a single heteroatom selected from N, O and S, or two N heteroatoms, including quinolyl, furyl, and thienyl; where the substituent is selected from halo (i.e., F, Cl, Br, and I), nitro, $C_1$–$C_4$-alkyl or alkoxy, and aryl, aralkyl and cycloalkyl containing up to 10 carbon atoms; and wherein $R_2$ and $R_3$ may each also be $C_1$–$C_4$-alkyl or aralkyl or cycloalkyl containing up to 10 carbon atoms.

In preferred embodiments of the invention, the 5'-protecting group is trityl, monomethoxy trityl, dimethoxytrityl, trimethoxytrityl, 2-chlorotrityl, DATE, TBTr, Pixyl or Moxyl, with trityl, monomethoxy trityl, dimethoxy trityl, 9-phenylxanthine-9-yl (Pixyl) or 9-(p-methoxyphenyl)xanthine-9-yl (MOX) being more preferred, and with dimethoxy trityl being especially preferred.

In some preferred embodiments, the present invention provides methods for the preparation of a phosphorus-linked oligomer comprising the steps of:

a) providing a solid support;

b) attaching a 5'-O-protected nucleoside to the solid support;

c) contacting the protected 5'-hydroxyl of the nucleoside with a deprotecting reagent comprising a protic acid in a solvent to deprotect the 5'-hydroxyl of the nucleoside, the solvent being an aromatic solvent, an alkyl aromatic solvent, a halogenated aromatic solvent, a halogenated alkyl aromatic solvent, or an aromatic ether solvent;

d) reacting the deprotected 5'-hydroxyl with a 5'-protected activated phosphite compound to produce a phosphite linkage;

e) oxidizing or sulfurizing the phosphite linkage to form a phosphodiester, phosphorothioate, or phosphorodithioate linkage;

f) repeating steps c through e at least once for subsequent couplings of additional activated phosphite compounds, to produce the completed phosphorus-linked oligomer; and g) cleaving the oligomer from the solid support.

As used herein, the term "activated phosphite compound" is intended to include mono-, di- and polynucloside phosphoramidites.

As used herein, the term "5'-protected activated phosphite compound" is intended to include a 5'-protected mono-, di- and polynucleoside phosphoramidite, as is used in standard solid phase oligonucleotide synthesis.

In some preferred embodiments of the invention the phosphordiamidite is activated to nucleophilic attack by the 5' hydroxyl by use of an activating agent. It is believed that the activating agent displaces one of the amino groups from the phosphordiamidite, thereby rendering the phosphorus of the phosphordiamidite more susceptible to nucleophilic attack by the 5' hydroxyl group of the growing nucleotide chain. Any activating agent that can activate the phosphorous to nucleophilic attack without interacting with the growing nucleotide chain may be suitable for use with the present invention. One preferred activating agent is tetrazole. Some commonly used commercially available activating agents are thiotetrazole, nitrotetrazole, and N,N-diisopropylaminohydrotetrazolide. Other suitable activating agents are also disclosed in the above incorporated patents as well as in U.S. Pat. No. 4,725,677 and in Berner, S., Muhlegger, K., and Seliger, H., *Nucleic Acids Research* 1989, 17:853; Dahl, B. H., Nielsen, J. and Dahl, O., *Nucleic Acids Research* 1987, 15:1729; and Nielson, J. Marugg, J. E., Van Boom, J. H., Honnens, J., Taagaard, M. and Dahl, O., *J. Chem. Research* 1986, 26, all of which are herein incorporated by reference.

Phosphorus linked oligomers produced by the methods of the invention will preferably be hybridizable to a specific target oligonucleotide. Preferably, the phosphorus linked oligomers produced by the methods of the invention comprise from about 1 to about 100 monomer subunits. It is more preferred that such compounds comprise from about 10 to about 30 monomer subunits, with 15 to 25 monomer subunits being particularly preferred.

As will be recognized, the process steps of the present invention need not be performed any particular number of times or in any particular sequence. Additional objects, advantages, and novel features of this invention will become apparent to those skilled in the art upon examination of the following examples thereof, which are not intended to be limiting.

EXAMPLE 1

Synthesis of 5'-TTTTTTT-3' Phosphorothioate Heptamer 50 milligram (2 μmole) of 5'-O-dimethoxytritylthymidine bound to CPG (controlled pore glass) through an ester linkage is taken up in a glass reactor, and a toluene solution of 3% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile, and then a solution of acetic anhydride/lutidine/THF (1:1:8), and N-methyl imidazole/THF is added to cap any unreacted 5'-hydroxyl group. The product is washed with acetonitrile.

This complete cycle is repeated five more times to produce the completely protected thymidine heptamer. The carrier containing the compound is treated with 30% aqueous ammonium hydroxide solution for 90 minutes at room temperature. The aqueous solution is filtered, and concentrated under reduced pressure to give a phosphorothioate heptamer, TTTTTTT.

EXAMPLE 2

Synthesis of 5'-d(GACT)-3' Phosphorothioate Tetramer 50 milligram (2 μmole) of 5'-O-dimethoxytritylthymidine bound to CPG (controlled pore glass) through an ester linkage is taken up in a glass reactor, and a toluene solution of 3% dichloroacetic acid in toluene (volume/volume) is added to deprotect the 5'-hydroxyl group. The product is washed with acetonitrile. Then, a 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A solution of 3% dichloroacetic acid in toluene (volume/volume) is added to deprotect the 5'-hydroxyl group. The product is washed with acetonitrile. Then, a 0.2 M solution of $N^4$-benzoyl-5'-O-(4,4'-dimethoxytrityl)-2'-deoxycytidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap any unreacted 5'-hydroxyl group. The product is washed with acetonitrile.

A solution of 3% dichloroacetic acid in toluene (volume/volume) is added to deprotect the 5'-hydroxyl group. The product is washed with acetonitrile. Then, a 0.2 M solution of $N^6$-benzoyl-5'-O-(4,4'-dimethoxytrityl)-2'-deoxyadenosine-3'-O-(2-cyanoethyl N,N-diisopropylphosphoramidite) in anhydrous acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A solution of 3% dichloroacetic acid in toluene (volume/volume) is added to deprotect the 5'-hydroxyl group. The product is washed with acetonitrile. Then, a 0.2 M solution of $N^2$-isobutyryl-5'-O-(4,4'-dimethoxytrityl)-2'-deoxyguanosine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap any unreacted 5'-hydroxyl group. The product is washed with acetonitrile.

The carrier containing the compound is treated with 30% aqueous ammonium hydroxide solution for 90 minutes at room temperature and then incubated at 55° C. for 24 hour. The aqueous solution is filtered, and concentrated under reduced pressure to give a phosphorothioate tetramer of 5'-dG-dA-dC-T-3'.

EXAMPLE 3

Synthesis of Fully-Modified 5'-d (TCC-CGC-CTG-TGA-CAT-GCA-TT)-3' Phosphorothioate 20-mer The synthesis of the above sequence was performed on a Pharmacia OligoPilot II Synthesizer on a 620 μmole scale using the cyanoethyl phosphoramidites and Pharmacia's PRIMAR support. Detrylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, treated with 30% aqueous ammonium hydroxide solution for 90 minutes at room temperature and then incubated at 55° C. for 24 hours to give the product.

EXAMPLE 4

Synthesis of Fully-Modified 5'-d(GCC-CAA-GCT-GGC-ATC-CGT-CA)-3' Phosphorothioate 20-mer The synthesis of the above sequence was performed on a Pharmacia OligoPilot II Synthesizer on a 620 µmole scale using the cyanoethyl phosphoramidites and Pharmacia's primar support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, treated with 30% aqueous ammonium hydroxide solution for 90 minutes at room temperature and then incubated at 55° C. for 24 hours to give the product.

EXAMPLE 5

Synthesis of Fully-Modified 5'-d(GCG-TTT-GCT-CTT-CTT-CTT-GCG)-3' Phosphorothioate 21-mer The synthesis of the above sequence was performed on a Pharmacia OligoPilot II Synthesizer on a 620 µmole scale using the cyanoethyl phosphoramidites and Pharmacia's PRIMAR support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, treated with 30% aqueous ammonium hydroxide solution for 90 minutes at room temperature and then incubated at 55° C. for 24 hours to give the product.

EXAMPLE 6

Synthesis of Fully-Modified 5'-d(GTT-CTC-GCT-GGT-GAG-TTT-CA)-3' Phosphorothioate 20-mer The synthesis of the above sequence was performed on a Pharmacia OligoPilot II Synthesizer on a 620 µmole scale using the cyanoethyl phosphoramidites and Pharmacia's PRIMAR support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, treated with 30% aqueous ammonium hydroxide solution for 90 minutes at room temperature and then incubated at 55° C. for 24 hours to give the product.

EXAMPLE 7

Synthesis of Fully-Modified 5'-d(TCC-CGC-CTG-TGA)-2'-methoxyethyl-(CAT-GCA-TT)-3, Phosphorothioate 20-mer The synthesis of the above sequence was performed on a Milligen 8800 Synthesizer on a 282 µmole scale using cyanoethyl phosphoramidites and Pharmacia's PRIMAR support. Detritylation was performed using 3% dichloroacetic acid in toluene (volume/volume). Sulfurization was performed using a 0.4 M solution of phenylacetyl disulfide in acetonitrile:3-picoline (1:1 v/v) for 6 minutes. At the end of synthesis, the support was washed with acetonitrile, treated with 30% aqueous ammonium hydroxide solution for 90 minutes at room temperature and then incubated at 55° C. for 24 hours to give the product.

EXAMPLE 8

Synthesis of Fully-Modified 5'-d(TCC-CGC-CTG-TGA)-2'-methoxyethyl-(CAT-GCA-TT)-3, Phosphorothioate 20-mer The synthesis of the above sequence was performed on a Pharmacia OligoPilot II Synthesizer on a 250 µmole scale using the cyanoethyl phosphoramidites and Pharmacia's PRIMAR support. Detritylation was performed using 3% dichloroacetic acid in toluene (volume/volume). Sulfurization was performed using a 0.4 M solution of phenylacetyl disulfide in acetonitrile:3-picoline (1:1 v/v) for 6 minutes. At the end of synthesis, the support was washed with acetonitrile, treated with 30% aqueous ammonium hydroxide solution for 90 minutes at room temperature and then incubated at 55° C. for 24 hours to give the product.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the preparation of a linear phosphorus-linked oligomer comprising the steps of:
   (a) providing a solid support;
   (b) attaching a 5'-O-protected nucleoside to the solid support;
   (c) deprotecting the 5'-hydroxyl of the nucleoside with a deprotecting reagent comprising a protic acid in a solvent to deprotect the 5'-hydroxyl of the nucleoside, wherein the solvent consists essentially of an aromatic solvent, an alkyl aromatic solvent, a halogenated aromatic solvent, a halogenated alkyl aromatic solvent, or an aromatic ether solvent;
   (d) reacting the deprotected 5'-hydroxyl with an 5'-protected activated phosphorus compound to produce a covalent linkage therebetween;
   (e) oxidizing or sulfurizing the covalent linkage to form a phosphodiester, phosphorothioate, phosphorodithioate or H-phosphonate linkage;
   (f) repeating steps c through e at least once for subsequent couplings of additional activated phosphorus compounds, to produce the completed phosphorus-linked oligomer; and
   (g) cleaving the oligomer from the solid support;
wherein steps (b) through (f) are performed with an automated device;
   wherein said oligomer is a linear oligomer.

2. The method of claim 1 further comprising the step of capping remaining reactive sites with a solution containing a capping reagent either immediately before said covalent linkage is oxidized or sulfurized or immediately after said covalent linkage is oxidized or sulfurized.

3. The method of claim 1 wherein the oxidation or sulfurization step is performed after each iteration of steps (c) and (d).

4. The method of claim 1 wherein the oxidation or sulfurization step is performed after the final iteration of steps (c) and (d).

5. The method of claim 1 wherein the solvent in step (c) is an aromatic solvent, an alkyl aromatic solvent, or an aromatic ether.

6. The method of claim 1 wherein the solvent in step (c) is selected from the group consisting of o-xylene, m-xylene, p-xylene, mesitylene, and diphenyl ether.

7. The method of claim 6 wherein the solvent in step (c) is selected from the group consisting of benzene, toluene, o-xylene, m-xylene, and p-xylene.

8. The method of claim 7 wherein the solvent in step (c) is toluene.

9. The method of claim 1 wherein the solvent in step (c) is a halogenated aromatic solvent or a halogenated alkyl aromatic solvent.

10. The method of claim 9 wherein the solvent in step (c) is chlorobenzene or benzotrifluoride.

11. The method of claim 1 wherein the activated phosphorus compound is selected from the group consisting of an activated mononucleotide, an activated dinucleotide, and an activated polynucleotide.

12. The method of claim 1 wherein the activated phosphorus compound is a 5'-protected nucloside phosphoramidite or a 5'-protected activated H-phosphonate nucleoside.

13. The method of claim 1 wherein the protecting group of the 5'-O-protected nucleoside and the 5'-protected activated phosphite compound is independently selected from the group consisting of trityl, monomethoxy trityl, dimethoxytrityl, trimethoxytrityl, 2-chlorotrityl, 1,1-dianisyl-2,2,2-trichloroethyl (DATE), 4,4',4"-tris(benzoyloxyphenyl)methyl (TBTr), 9-phenylxanthine-9-yl (Pixyl) and 9-(p-methoxyphenyl)xanthine-9-yl (MOX).

14. The method of claim 13 wherein the protecting group of the 5'-O-protected nucleoside and the 5'-protected activated phosphite compound is independently selected from the group consisting of trityl, monomethoxy trityl, dimethoxy trityl, 9-phenylxanthine-9-yl (Pixyl) and 9-(p-methoxyphenyl)xanthine-9-yl.

15. The method of claim 14 wherein the protecting group of the 5'-O-protected nucleoside and the 5'-protected activated phosphite compound is dimethoxytrityl.

16. The method of claim 1 wherein the phosphorus-linked oligomer is selected from the group consisting of a phosphodiester, a phosphorothioate phosphorodithioate, and a H-phosphonate oligonucleotide.

17. The method of claim 1 wherein the protic acid is selected from the group consisting of formic acid, acetic acid, chloroacetic acid, dichloroacetic acid, trichloroacetic acid, trifluoroacetic acid, benzenesulfonic acid, toluenesulfonic acid, and phenylphosphoric acid.

18. The method of claim 1 wherein the solvent in step (c) further comprises an additive.

19. The method of claim 18 wherein the additive to the solvent in step (c) is an alcohol.

20. The method of claim 19 wherein the alcohol additive to the solvent in step (c) is selected from the group consisting of from 0% to about 30% methanol, ethanol, 2-propanol, t-butyl alcohol, t-amyl alcohol, benzyl alcohol, 1,1,1,3,3,3-hexafluoro-2-propanol, and mixtures thereof.

21. A method for the preparation of a linear phosphorus-linked oligomer comprising the steps of:
(a) providing a solid support;
(b) attaching a 5'-O-protected nucleoside to the solid support;
(c) contacting the protected 5'-hydroxyl of the nucleoside with a deprotecting reagent comprising a protic acid in a solvent to deprotect the 5'-hydroxyl of the nucleoside, wherein the solvent consists essentially of an aromatic solvent, an alkyl aromatic solvent, a halogenated aromatic solvent, a halogenated alkyl aromatic solvent, or an aromatic ether solvent;
(d) reacting the deprotected 5'-hydroxyl with a 5'-protected activated phosphite compound to produce a phosphite linkage;
(e) oxidizing or sulfurizing the phosphite linkage to form a phosphodiester, phosphorothioate, or phosphorodithioate linkage;
(f) repeating steps c through e at least once for subsequent couplings of additional activated phosphite compounds, to produce the completed phosphorus-linked oligomer; and
(g) cleaving the oligomer from the solid support;
wherein steps (b) through (f) are performed with an automated device;
wherein said oligomer is a linear oligomer.

22. The method of claim 21 further comprising the step of capping remaining reactive sites with a solution containing a capping reagent either immediately before said covalent linkage is oxidized or sulfurized or immediately after said covalent linkage is oxidized or sulfurized.

23. The method of claim 21 wherein the solvent in step (c) is selected from the group consisting of an aromatic solvent, an alkyl aromatic solvent, and an aromatic ether.

24. The method of claim 23 wherein the solvent in step (c) is selected from the group consisting of benzene, toluene, benzonitrile, o-xylene, m-xylene, p-xylene, mesitylene, and diphenyl ether.

25. The method of claim 24 wherein the solvent in step (c) is selected from the group consisting of benzene, toluene, o-xylene, m-xylene, and p-xylene.

26. The method of claim 25 wherein the solvent in step (c) is toluene.

27. The method of claim 21 wherein the solvent in step (c) is a halogenated aromatic solvent or a halogenated alkyl aromatic solvent.

28. The method of claim 27 wherein the solvent in step (c) is chlorobenzene or benzotrifluoride.

29. The method of claim 21 wherein the activated phosphite compound is selected from the group consisting of a mononucleotide phosphoramidite, a dinucleotide phosphoramidite, and a polynucleotide phosphoramidite.

30. The method of claim 21 wherein the protecting group of the 5'-O-protected nucleoside and the 5'-protected activated phosphite compound is independently selected from the group consisting of trityl, monomethoxy trityl, dimethoxytrityl, trimethoxytrityl, 2-chlorotrityl, 1,1-dianisyl-2,2,2-trichloroethyl (DATE), 4,4',4"-tris(benzoyloxyphenyl)methyl (TBTr), 9-phenylxanthine-9-yl (Pixyl) and 9-(p-methoxyphenyl)xanthine-9-yl (MOX).

31. The method of claim 30 wherein the protecting group of the 5'-O-protected nucleoside and the 5'-protected activated phosphite compound is independently selected from the group consisting of trityl, monomethoxy trityl, dimethoxy trityl, 9-phenylxanthine-9-yl (Pixyl) and 9-(p-methoxyphenyl)xanthine-9-yl.

32. The method of claim 31 wherein the protecting group of the 5'-O-protected nucleoside and the 5'-protected activated phosphite compound is dimethoxytrityl.

33. The method of claim 21 wherein the phosphorus-linked oligomer is selected from the group consisting of a phosphodiester, phosphorothioate and a phosphorodithioate oligonucleotide.

34. The method of claim 21 wherein the protic acid is selected from the group consisting of formic acid, acetic acid, chloroacetic acid, dichloroacetic acid, trichloroacetic acid, trifluoroacetic acid, benzenesulfonic acid, toluenesulfonic acid, and phenylphosphoric acid.

35. The method of claim 21 wherein the solvent in step (c) further comprises an additive.

36. The method of claim 35 wherein the additive to the solvent in step (c) is an alcohol.

37. The method of claim 36 wherein the alcohol additive to the solvent in step (c) is selected from the group consisting of from 0% to about 30% methanol, ethanol, 2-propanol, t-butyl alcohol, t-amyl alcohol, benzyl alcohol, 1,1,1,3,3,3-hexafluoro-2-propanol, and mixtures thereof.

38. The method of claim 22 wherein the solvent in step (c) is selected from the group consisting of benzene, toluene, benzonitrile, o-xylene, m-xylene, p-xylene, mesitylene, and diphenyl ether; the activated phosphite compound is selected from the group consisting of a mononucleotide phosphoramidite, a dinucleotide phosphoramidite, and a polynucleotide phosphoramidite; the protecting group of the 5'-O-protected nucleoside and the 5'-protected activated phosphite compound is dimethoxytrityl; the phosphorus linked oligomer is selected from the group consisting of a phosphodiester, phosphorothioate and a phosphorodithioate oligonucleotide; and the protic acid is dichloroacetic acid.

39. The method of claim 38 wherein the solvent in step (c) is toluene.

40. The method of claim 39 wherein the activated phosphite compound is a mononucleotide phosphoramidite.

41. The method of claim 1 wherein the 5'-protected activated phosphorus compound is a 5'-protected activated H-phosphonate compound; and the phosphorus-linked oligomer is an H-phosphonate oligonucleotide.

42. A method for the preparation of a linear phosphorus-linked oligomer comprising the steps of:
    (a) providing a solid support;
    (b) attaching a 5'-O-protected nucleoside to the solid support;
    (c) deprotecting the 5'-hydroxyl of the nucleoside with a deprotecting reagent comprising dichloroacetic acid in toluene;
    (d) reacting the deprotected 5'-hydroxyl with an 5'-protected activated phosphorus compound to produce a covalent linkage therebetween;
    (e) oxidizing or sulfurizing the covalent linkage to form a phosphodiester, phosphorothioate, phosphorodithioate or H-phosphonate linkage;
    (f) repeating steps c through e at least once for subsequent couplings of additional activated phosphorus compounds, to produce the completed phosphorus-linked oligomer; and
    (g) cleaving the oligomer from the solid support;
wherein steps (b) through (f) are performed with an automated device;
wherein said oligomer is a linear oligomer.

* * * * *

UNITED STATES PATENT AND TRADEMARK OFFICE
CERTIFICATE OF CORRECTION

PATENT NO. : 7,273,933 B1 Page 1 of 1
APPLICATION NO. : 09/032972
DATED : September 25, 2007
INVENTOR(S) : Achim H. Krotz and Vasulinga T. Ravikumar It is certified that error appears in the above-identified patent and that said Letters Patent is hereby corrected as shown below:

1) Title Page:
Item [56], References Cited, OTHER PUBLICATIONS, "Krotz" reference, please delete "Mar. 1, 1996" and insert therefor --Mar. 18, 1996--.

Signed and Sealed this

Thirteenth Day of November, 2007

JON W. DUDAS
*Director of the United States Patent and Trademark Office*